s011235177B2

United States Patent
Krishnaswamy et al.

(10) Patent No.: US 11,235,177 B2
(45) Date of Patent: Feb. 1, 2022

(54) ADVANCED CHERENKOV-BASED IMAGING SYSTEMS, TOOLS, AND METHODS OF FEEDBACK CONTROL, TEMPORAL CONTROL SEQUENCE IMAGE CAPTURE, AND QUANTIFICATION IN HIGH RESOLUTION DOSE IMAGES

(71) Applicants: DOSEOPTICS LLC, Lebanon, NH (US); Venkataramanan Krishnaswamy, Lebanon, NH (US); Brian W. Pogue, Hanover, NH (US)

(72) Inventors: Venkataramanan Krishnaswamy, Lebanon, NH (US); Brian W. Pogue, Hanover, NH (US)

(73) Assignee: DoseOptics LLC, Lebanon, NH (US)

( * ) Notice: Subject to any disclaimer, the term of this patent is extended or adjusted under 35 U.S.C. 154(b) by 0 days.

(21) Appl. No.: 16/344,139

(22) PCT Filed: Oct. 23, 2017

(86) PCT No.: PCT/US2017/057836
§ 371 (c)(1),
(2) Date: Apr. 23, 2019

(87) PCT Pub. No.: WO2018/076004
PCT Pub. Date: Apr. 26, 2018

(65) Prior Publication Data
US 2020/0061391 A1    Feb. 27, 2020

Related U.S. Application Data

(60) Provisional application No. 62/411,673, filed on Oct. 23, 2016.

(51) Int. Cl.
*A61N 5/10* (2006.01)
*G01T 1/22* (2006.01)

(52) U.S. Cl.
CPC ......... *A61N 5/1075* (2013.01); *A61N 5/1067* (2013.01); *A61N 5/1071* (2013.01); *G01T 1/22* (2013.01)

(58) Field of Classification Search
CPC .......... A61N 5/1071; A61N 2005/1054; A61N 2005/1059; A61N 5/1049; A61N 5/1065;
(Continued)

(56) References Cited

U.S. PATENT DOCUMENTS 10,569,105 B2 *  2/2020  Kilby ................... A61B 6/583
2016/0263402 A1 *  9/2016  Zhang ................. A61N 5/1071
(Continued)

*Primary Examiner* — David A Vanore
(74) *Attorney, Agent, or Firm* — JWIP & Patent Services, LLC; Jacob G. Weintraub, Esq.

(57) ABSTRACT

The present invention relates to advanced Cherenkov-based imaging systems, tools, and methods of feedback control, temporal control sequence image capture, and quantification in high resolution dose images. In particular, the present invention provides a system and method for simple, accurate, quick, robust, real-time, water-equivalent characterization of beams from LINACs and other systems producing external-therapy radiation for purposes including optimization, commissioning, routine quality auditing, R&D, and manufacture. The present invention also provides a system and method for rapid and economic characterization of complex radiation treatment plans prior to patient exposure. Further, the present invention also provides a system and method of economically detecting Cherenkov radiation emitted by tissue and other media in real-world clinical settings (e.g., settings illuminated by visible light).

6 Claims, 10 Drawing Sheets

(58) Field of Classification Search
CPC .. A61N 5/1075; A61N 5/1081; A61N 5/1083; A61N 2005/1076; A61N 2005/1091; A61N 5/1043; A61N 5/1045; A61N 5/1077; A61N 5/1067; A61N 5/00; A61N 5/10; A61B 6/583; A61B 5/0071; A61B 5/0077; A61B 5/7292; A61B 6/542; G01T 1/22; G01T 1/10
See application file for complete search history.

(56) References Cited

U.S. PATENT DOCUMENTS

| | | | |
|---|---|---|---|
| 2017/0252579 A1* | 9/2017 | Kilby | A61N 5/1075 |
| 2020/0057165 A1* | 2/2020 | Archambault | A61B 6/542 |
| 2020/0346041 A1* | 11/2020 | Krishnaswamy | A61N 5/1081 |

* cited by examiner

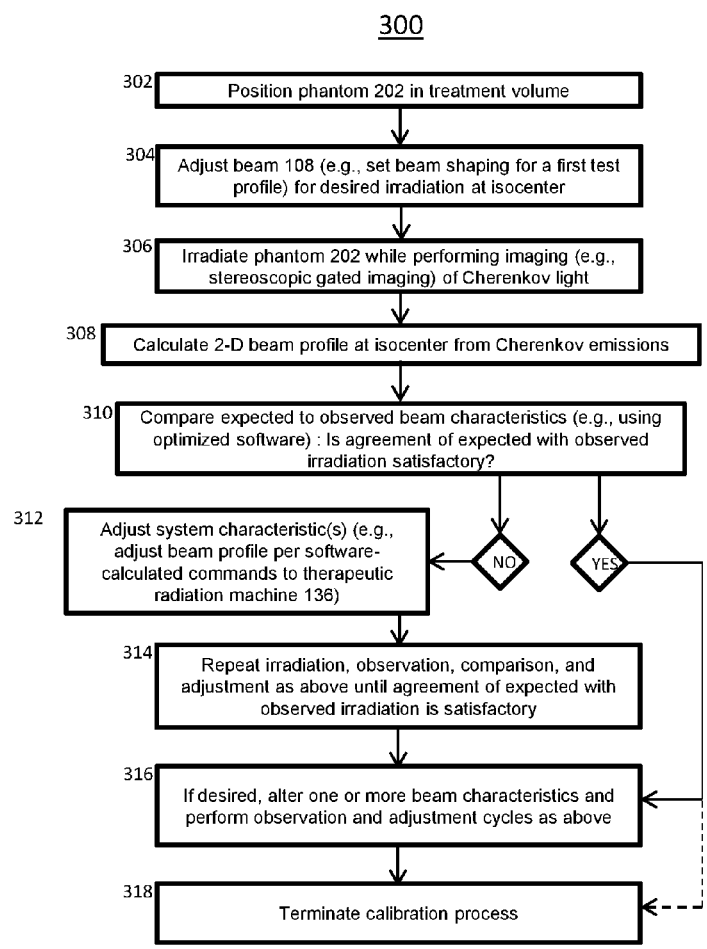

ADVANCED CHERENKOV-BASED IMAGING SYSTEMS, TOOLS, AND METHODS OF FEEDBACK CONTROL, TEMPORAL CONTROL SEQUENCE IMAGE CAPTURE, AND QUANTIFICATION IN HIGH RESOLUTION DOSE IMAGES

RELATED APPLICATIONS

This application claims priority to U.S. Provisional Patent Application No. 62/411,673, filed on Oct. 23, 2016; the entirety of which is incorporated herein by reference.

GOVERNMENT INTEREST

The invention herein has been supported by grants awarded by the National Institutes of Health, grant numbers R01 CA109558 and R43 CA199681, and F31 CA192473. The Government has certain rights to the inventions.

BACKGROUND OF THE INVENTION

High-energy particle beams or high-energy photon beams are used in the treatment of many cancers. Such beams are typically provided by a linear accelerator (LINAC), or related apparatus. When treating cancers with radiation it is desirable to target the beam in time and space such that there is a high net ratio of energy deposited in the tumor relative to energy deposited in normal tissues outside the tumor, resulting in a high therapeutic ratio of tumor to nominal dose.

Further, when treating patients with a high-energy radiation beam it is desirable to verify that the beam shape is as planned. Additionally, when beams enter tissue it is important to accurately predict how radiation beam shape varies with depth in tissue, to ensure adequate dosage to tumor tissue while minimizing dosage to surrounding normal tissues. Thus, if beam shape and orientation are adjusted by positioning deflection magnets or shielding devices, it can be important to confirm that the resulting beam shape and dosage profile are as desired prior to exposing patients to the beam; radiation treatment centers may therefore desire to confirm beam shape and dose profile for complex beam shaping procedures for each patient or as part of routine calibration and maintenance. Moreover, there is occasion to verify the aiming, shaping, timing, and other characteristics of therapeutic radiation beams during routine quality assurance or quality audit and recalibration of treatment systems and prior to the administration of treatment plans to patients, where inadvertent exposure of all non-tumor tissue to radiation must be minimized.

In fact, manufacturers of radiation treatment devices routinely prepare documentation of beam shapes and dosage profiles produced by common configurations of their devices for training users and guiding operators in using their machines to treat patients. Further, they must seek regulatory approvals of their machines, and as part of the regulatory approvals process are expected to provide documentation of beam shapes and dosage profiles achievable by their machines. Manufacturers may therefore also need to accurately verify and document beam profiles for this regulatory approval process.

Although Cherenkov light emitted by tissue or by media with radiological properties similar to those of tissue (such as water) can be advantageously employed as a proxy for radiation delivered to tissue and to other media, its real-time use for beam construction has been elusive with current technology. Moreover, Cherenkov light has found use for qualitative applications, in systems that detect Cherenkov radiation emitted by tissue and other media in real-world clinical settings, however, via costly detection methodology.

As such, there is a need for a system and method for simple, accurate, quick, robust, real-time characterization of beams from LINACs and other systems producing external-therapy radiation for purposes including optimization, commissioning, routine quality auditing, R&D, and manufacture. There is also need for a system and method for rapid and economic characterization of complex radiation treatment plans prior to patient exposure. There is a further need for a system and method of economically detecting Cherenkov radiation emitted by tissue and other media in real-world clinical settings (e.g., settings illuminated by visible light).

SUMMARY OF THE INVENTION

Accordingly, the present invention is directed to advanced Cherenkov-based imaging systems, tools, and methods of feedback control, temporal control sequence image capture, and quantification in high resolution dose images. In particular, the present invention provides a system and method for simple, accurate, quick, robust, real-time, water-equivalent characterization of beams from LINACs and other systems producing external-therapy radiation for purposes including optimization, commissioning, routine quality auditing, R&D, and manufacture. The present invention also provides a system and method for rapid and economic characterization of complex radiation treatment plans prior to patient exposure. Further, the present invention also provides a system and method of economically detecting Cherenkov radiation emitted by tissue and other media in real-world clinical settings (e.g., settings illuminated by visible light).

As such, one aspect of the present invention provides a direct feedback interface (DFI) control unit comprising a machine-readable medium having instructions stored thereon for execution by a processor to perform a method. The method comprises the steps of: detection of Cherenkov radiation after exposure of a subject to high-energy radiation from a radiation beam source; creation of an image; comparative analysis of the image to a reference image; and communication of the results of the comparative analysis to the radiation beam source unit, wherein such communication is capable of instructing modification of the beam profile.

In another aspect, the present invention provides an advanced Cherenkov-based imaging system comprising: a radiation beam source; at least one camera capable of imaging Cherenkov radiation; one or more processing units that enables the control of the radiation beam source; and a direct feedback interface (DFI) control unit, wherein the Cherenkov radiation is detected by the camera after exposure of a subject to high-energy radiation from the radiation beam source.

An additional aspect of the present invention provides a quantifier integration (QI) unit comprising a machine-readable medium having instructions stored thereon for execution by a processor to perform a method. The method comprises the steps of: detection of Cherenkov radiation after exposure of a subject to high-energy radiation from a radiation beam source, and establishment of a Cherenkov radiation image; detection of non-Cherenkov radiation after exposure of a subject to high-energy radiation from a radiation beam source, and establishment of a non-Cherenkov radiation measurement; and integration of the non-Cherenkov radiation measurements with the Cherenkov radiation image, to produce a quantitatively calibrated high resolution Cherenkov image.

In yet another aspect, the present invention provides an advanced Cherenkov-based imaging system comprising: a radiation beam source; at least one camera capable of imaging Cherenkov radiation; one or more processing units that enables the control of the radiation beam source; a non-Cherenkov radiation measurement device; and a quantifier integration unit, wherein the Cherenkov radiation is detected by the camera and non-Cherenkov radiation is detected by the non-Cherenkov radiation measurement device after exposure of a subject to high-energy radiation from the radiation beam source.

Another aspect of the present invention provides a speed gating unit employing a temporal control sequence comprising a machine-readable medium having instructions stored thereon for execution by a processor to perform a method. The method comprises the steps of: controlling the temporal sequence gating of lighting in a room; and controlling the temporal sequence gating of the exposure of at least one camera capable of imaging Cherenkov radiation upon exposure of a subject to high-energy radiation from the radiation beam source, such that the gating of lighting and the camera exposure are pulsed at millisecond speed.

An additional aspect of the present invention provides an advanced Cherenkov-based imaging system comprising: a radiation beam source; at least one camera capable of imaging Cherenkov radiation; one or more processing units that enables the control of the radiation beam source; one or more illumination devices for use in room lighting; and a speed gating unit employing a temporal control sequence designed to complimentarily control the temporal sequence gating of the room lighting and the camera exposure, wherein the speed gating of each is pulsed at millisecond speed, wherein the Cherenkov radiation is detected by the camera after exposure of a subject to high-energy radiation from the radiation beam source.

BRIEF DESCRIPTION OF THE DRAWINGS

Advantages of the present apparatus will be apparent from the following detailed description, which description should be considered in combination with the accompanying drawings, which are not intended limit the scope of the invention in any way.

In the drawings, like reference characters generally refer to the same parts throughout the different views. In this respect, it is to be understood that the invention is not limited in its application to the details of construction and to the arrangements of the components set forth in the following description or illustrated in the drawings. The invention is capable of other embodiments and of being practiced and carried out in various ways. Also, the drawings are not necessarily to scale, emphasis instead generally being placed upon illustrating certain principles of the invention. In the following description, various embodiments of the present invention are described with reference to the following drawings, in which:

FIG. 3 is a flow chart of an illustrative method of operation of the system of FIG. 2.

DETAILED DESCRIPTION OF THE INVENTION

Figure 1A:
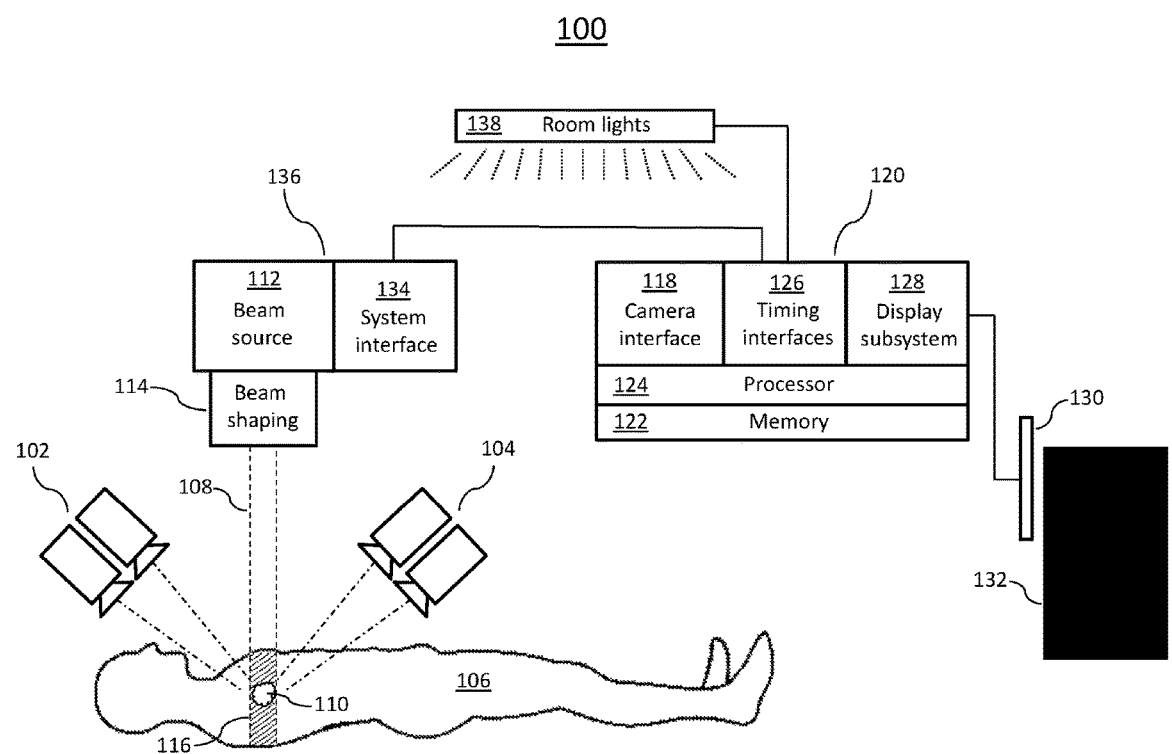
FIG. 1A schematically depicts an illustrative system for performing monitored radiotherapy with time-controlled room lighting and camera sensing of light emissions from a subject.

The present invention is directed to advanced Cherenkov-based imaging systems, tools, and methods of feedback control, temporal control sequence image capture, and quantification in high resolution dose images. In accordance with certain embodiments, systems and methods are disclosed that enable (1) rapid and thorough optimization, quality auditing, commissioning, and characterization of beams from LINACs and other systems producing external-therapy radiation, (2) rapid and economic characterization of complex radiation treatment plans prior to patient exposure, and (3) economical detection of Cherenkov radiation emitted by tissue and other media such as water in real-world clinical settings (e.g., settings illuminated by visible light) by means of spectral and temporal modulation of illumination and light detection.

In this respect, it is known that charged particles (e.g., electrons, positrons, protons, alpha particles) moving faster than the speed of light in a dielectric medium v decelerate while emitting photons. These photons are termed Cherenkov (a.k.a. "Cerenkov" and similar spellings) radiation. In particular, charged particles moving with sufficient speed cause emission of Cherenkov radiation in human tissue. Similarly, water is another medium in which the speed of light is less than c and in which fast-moving charged particles induce Cherenkov radiation. Cherenkov radiation can also result from irradiation by high-energy photons used in cancer therapy (e.g., 6-18 MV), because Compton scatter of these produce secondary electron emission having sufficient kinetic energy to produce Cherenkov radiation in the medium. Cherenkov emission in human tissue has been detected with incident radiation in the range of 6 to 24 MeV energies for electrons and x-ray photons. Since Cherenkov emission depends on particle velocity, more-massive particles (e.g., protons, alpha particles) must have correspondingly higher energies in order to produce Cherenkov radiation in a given dielectric medium, and so Cherenkov is only emitted from larger-mass radiation such as protons at considerably higher kinetic energy. Although no particle of nonzero mass can move at or above velocity c, it is common that particle velocities can exceed v in material media when excited to kinetic energies greater than a few hundred kiloelectron volts (keV).

Cherenkov radiation (or "Cherenkov light") is emitted at an acute angle θ to the path of a particle moving at velocity $v_p$, where $\cos \theta = c/(nv_p)$ and n is the refractive index of the medium; when numerous charged particles move at suitable velocity in a collimated beam, a Cherenkov glow is emitted in a conic pattern at angle θ to the beam, which is approximately 41 degrees from the direction of travel. Cherenkov emission has a continuous spectrum across the entire ultraviolet, visible, and near-infrared spectrum with intensity varying as the inverse square of the wavelength (up to a cutoff frequency). Thus, Cherenkov emission at higher frequencies (shorter wavelengths) is more intense, giving rise to Cherenkov light's characteristic blue color when viewed by eye or camera.

When Cherenkov light is induced locally inside water or tissue, it is predominantly blue in color, but with a broad spectrum which tapers off into the green, red, and near-infrared (NIR) with an inverse square wavelength dependence given by the Frank-Tamm formula. This light when emitted within tissue is attenuated by absorbers significantly reducing the blue green wavelengths and largely just leaving the red and NIR wavelengths for transmission over a few millimeters. This light in the tissue can also excite other molecular species within the tissue to induce photo-luminescence (i.e., fluorescence or phosphorescence).

Cherenkov light is of significance for medical radiation systems because its intensity at any given point in a volume of tissue, as captured by imaging equipment, correlates with the intensity at that point of radiation that meets the criteria for inducing Cherenkov light. Cherenkov light emission is thus a proxy for high-energy radiation intensity. Therefore, Cherenkov light enables qualitative and relative observation of a high-energy radiation beam by an imaging device (e.g., camera) not aligned directly with the beam and thus not subject to damage by it.

Accordingly, herein are disclosed systems, tools, and methods for the enhancement of therapeutic radiation dosimetry using aspects of Cherenkov light emission from a standard linear accelerator, including the emission of fluorescent light from fluorophores stimulated by Cherenkov light. In certain embodiments of the invention, operative feedback including Cherenkov imaging, e.g., of a phantom (nonliving test object), is employed to enable a human operator or computational system to adjust a therapeutic radiation machine or plan of treatment for purposes of design, commissioning, quality auditing, adjustment, treatment plan verification, or the like in real-time. In certain other embodiments of the invention, localized high-accuracy measurements of therapeutic radiation flux by an additionally available measurement device (e.g., by external portal imaging device, ionization chamber, or diode) are integrated with Cherenkov imaging to produce Cherenkov visualizations of dose delivery (tomographic or otherwise enhanced characterizations of therapeutic radiation beam profiles) calibrated to accurate dose units, i.e., high resolution dose images described herein. In certain other embodiments, Cherenkov imaging is enhanced by applying temporal and/or spectral selectivity to the emission and/or sensing of illuminative ambient light in order increase the detectability of Cherenkov light and removal of background room light signals.

The present invention, including advanced Cherenkov-based imaging systems, tools, and related methods will be described with reference to the following definitions that, for convenience, are set forth below. Unless otherwise specified, the below terms used herein are defined as follows:

I. Definitions

As used herein, the term "a," "an," "the" and similar terms used in the context of the present invention (especially in the context of the claims) are to be construed to cover both the singular and plural unless otherwise indicated herein or clearly contradicted by the context.

The term "camera" is used herein to describe a camera capable of imaging Cherenkov radiation (and/or radiation emitted by fluorescent substances (fluorophores) excited by Cherenkov radiation).

The term "interface" is art-recognized, and is used herein to describe a shared boundary across which two separate components of a computer system exchange information, which can be between software, computer hardware, peripheral devices, humans and combinations of these. Moreover, the operation of two separate components across the boundary, as in the interaction of the camera interface which is designed to interface with the camera, is referred to herein as "interfacing." In certain embodiments, the interfacing may be bi-directional. In other embodiments, the interfacing may be uni-directional. In specific embodiments, the term "interface" may be a user interface, e.g., a graphic user interface.

The language "high-energy radiation" is used herein to describe radiation that, considering the mass of the particle being accelerated contains enough energy to generate Cherenkov radiation upon entry into a given medium, with given refractive index. As such, the use of the language "high-energy radiation" herein takes into account both the delivered particle and the medium being irradiated.

The term "isocenter" is art-recognized, and is used in herein to describe the point in space relative to the treatment machine which indicates the center of the treatment volume, e.g., in a system where various components of the system rotate, the isocenter is the point about which the components rotate. Location of the radiation isocenter plays an important role in treatment planning, since ideally the isocenter should be placed in the center of the target volume (e.g., a tumor); thus, patient positioning with respect to the isocenter is a significant factor for the successful irradiation of cancerous tissue and consequently for treatment outcome.

The language "machine-readable medium" is art-recognized, and describes a medium capable of storing data in a format readable by a mechanical device (rather than by a human). Examples of machine-readable media include magnetic media such as magnetic disks, cards, tapes, and drums, punched cards and paper tapes, optical disks, barcodes, magnetic ink characters, and solid state devices such as flash-based, SSD, etc. Machine-readable medium of the present invention are non-transitory, and therefore do not include signals per se, i.e., are directed only to hardware storage medium. Common machine-readable technologies include magnetic recording, processing waveforms, and barcodes. In particular embodiments, the machine-readable device is a solid state device. Optical character recognition (OCR) can be used to enable machines to read information available to humans. Any information retrievable by any form of energy can be machine-readable. Moreover, any data stored on a machine-readable medium may be transferred by streaming over a network. In a particular embodiment, the machine-readable medium is a network server disk, e.g., an internet server disk, e.g., a disk array. In specific embodiments, the machine-readable medium is more than one network server disks.

The term "subject" as used herein is to described the object being irradiated with radiation, e.g., a phantom or human tissue (e.g., a human)

The term "user" or "operator" are used interchangeably herein to describe any person that operates the systems of the present invention, e.g., interfaces with the user interface of the present invention.

II. Advancements in Cherenkov-Based Imaging Systems

Cherenkov-based imaging systems have been shown to be capable of offering instantaneous radiation surface imaging of a subject exposed with certain high-energy radiation, in order to record and verify the accuracy of the qualitative treatment at the time of exposure and upon entry into the subject, e.g., phantom or patient. Such systems generally comprise a radiation beam source and at least one camera capable of imaging Cherenkov light, and a machine re machine-readable medium designed to record/store the information.

In contrast, the advanced Cherenkov-based imaging systems of the present invention further provide enhanced system features that afford the systems themselves the ability to more actively utilize this information through (1) feedback presentation of this information to control the radiation beam source; (2) quantification of dose based on Cherenkov imaging, providing high resolution images; and (3) improved dynamic range image capture through utilization of temporal control sequences, which are more economical than conventional means.

As such, one embodiment of the present invention provides an advanced Cherenkov-based imaging system comprising:
- a radiation beam source (e.g., a particle accelerator or other device for providing high-energy radiation, which, for example, may be cross-sectionally shaped by a beam-shaping apparatus, e.g., a multi-leaf collimator);
- at least one camera capable of imaging Cherenkov radiation (and/or radiation emitted by fluorescent substances (fluorophores) excited by Cherenkov radiation); and
- one or more processing units that enables the control of the radiation beam source,
- wherein the Cherenkov radiation is detected by the camera after exposure of a subject to high-energy radiation from the radiation beam source. In certain embodiments, systems of the present invention have desirable properties such as rapidity, three- and four-dimensionality, and water equivalence.

In certain embodiments of the present invention, the systems further comprise an illumination system adapted to substantially reduce (e.g., eliminate) red and infrared light/radiation. In particular embodiments, this is accomplished using an LED illumination system.

Figure 1B:
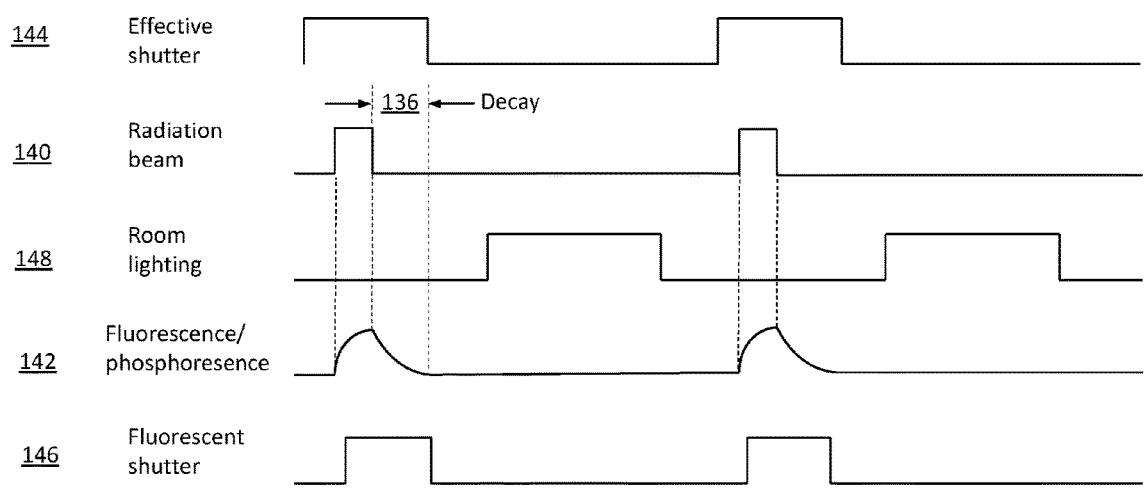
FIG. 1B is a diagram showing the approximate relationships of room lighting, beam pulses, light emissions, and camera shutter windows in one mode of operation of the system of FIG. 1A.
Figure 2:
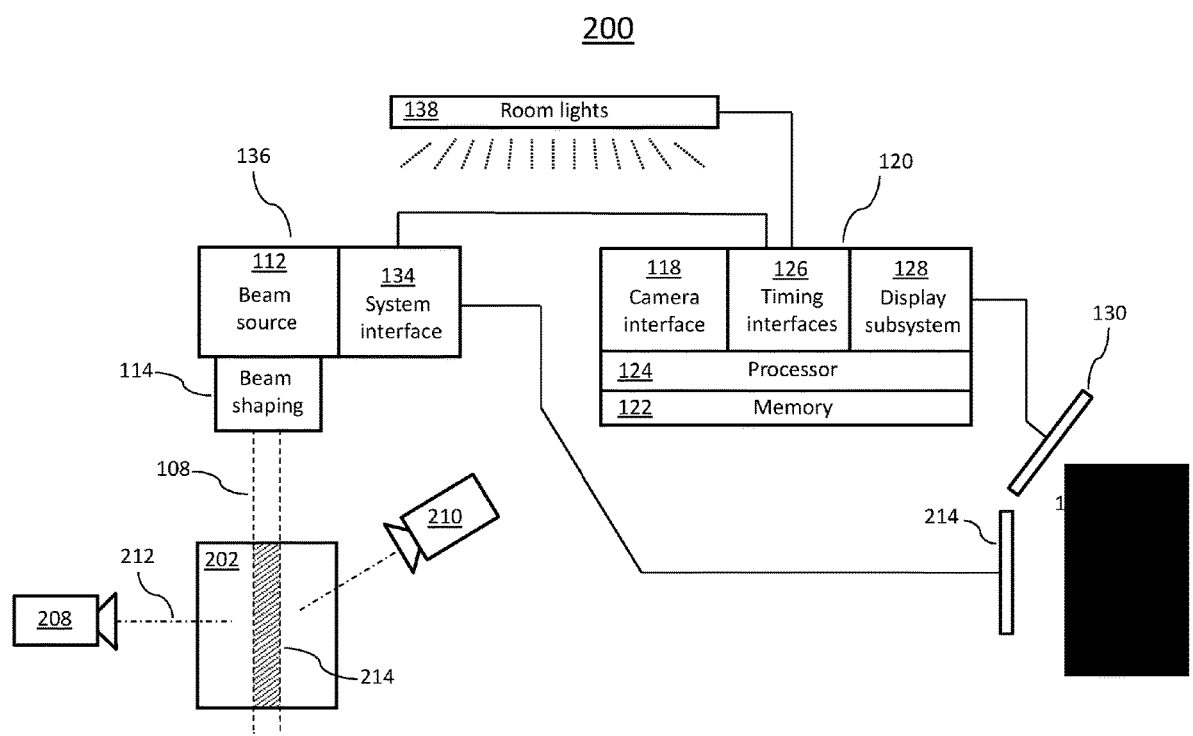
FIG. 2 is a schematic block diagram of an apparatus for coordinated direct feedback observation and adjustment/control of high-energy beam profiles in a therapeutic radiation system while imaging the beam depositing dose in a phantom.

FIG. 1A, FIG. 1B, and FIG. 2, described further herein below, depict certain aspects of systems that are relevant to various embodiments of the invention.

FIG. 1A schematically depicts portions of an illustrative external-beam radiation therapy system 100 similar to a system shown and described in U.S. Provisional Patent Application No. 62/153,417, filed on Apr. 27, 2015, and entitled "CHERENKOV IMAGING SYSTEMS AND METHODS FOR DETERMINING RADIATION DOSE," the disclosure of which is hereby incorporated herein in its entirety by reference. System 100 provides context relevant to various embodiments of the invention described herein. In particular, system 100 depicts high-sensitivity electronic cameras or groups of cameras 102, 104 that are used to image Cherenkov light and/or light emitted by fluorescent substances (fluorophores) excited by Cherenkov light and to localize locations on or in a human subject 106 where this light is emitted. In certain embodiments, the subject 106 is preferably located within an environment from which light from uncontrolled sources, such as the sun and incandescent lamps, is excluded or minimized. In certain embodiments of the system 100 depicted in FIG. 1A, the subject 106 is placed in the path of a radiation beam 108 so that the beam 108 irradiates a tumor 110. Beam 108 is provided by a radiation beam source 112, e.g., a particle accelerator or other device for providing high-energy radiation, and typically is cross-sectionally shaped by a beam-shaping apparatus 114, e.g., a multi-leaf collimator.

In the illustrative system 100 of FIG. 1A, the source 112 is an accelerator that provides a beam 108 of electrons having energy of between 6 million electron volts (6 MeV) and 24 MeV, such as is used to deliver treatment energy to deep tumors as opposed to treatment of surface skin. Various other therapeutic systems could produce, for example, a photon beam of 6 MeV or higher or a high-energy proton beam. In general, various embodiments of the invention can be combined with a number of therapeutic radiation systems that produce beams capable of inducing Cherenkov radiation emission in human tissue, including but not limited to systems described explicitly herein.

In certain embodiments of the present invention, and various systems similar to system 100, cameras (e.g., cameras 102, 106) image the subject 106 from fewer or more points of view than are depicted in FIG. 1A, or non-stereoscopic cameras are used, or a single camera is arranged to move to more than one position with respect to the subject, or the subject 106 is supported in a manner that permits their rotation with respect to one or more cameras, or some combination of one or more of these or other imaging arrangements is employed. Cherenkov and/or fluorescent radiation emission occurs where the tissues (or tissue equivalent) of the subject 106 are irradiated by the beam 108, a volume herein termed the emission volume 116. Fluorescent light emissions can be induced by Cherenkov-light excitation of fluorophores in tissue, where such fluorophores are present, and are radiated isotropically rather than directionally as is the case with Cherenkov radiation.

In certain embodiments, the cameras 102, 104 are aimed to image at least part of the emission volume 116 and are coupled to a camera interface 118 of an image-processing system 120. Camera connections to the camera interface 118 may be wired or wireless and are not depicted in FIG. 1A for clarity. Herein, in certain embodiments, camera connections may serve both to transfer image data from a camera to the camera interface 118 and to convey commands (e.g., for setting shutter timing, exposure) from the camera interface 118 to the camera. In certain embodiments of the present invention, and various systems similar to system 100, light-modifying components such as filters and light intensifiers are aligned with cameras, or included in cameras, to intensify and/or selectively admit Cherenkov and/or fluorescence light; however, such light-modifying devices are omitted from FIG. 1A for simplicity. The camera interface 118 captures and stores digital images from the cameras 102, 104 in memory 122 for later retrieval and processing, e.g., processing by at least one processor 124 of the image processing system 120. The processor 124 can exchange information not only with the camera interface 118 and memory 122 but with a timing interface 126, a display subsystem 128, and potentially other devices as well. The display subsystem 128 communicates with a user interface 130 through which a user 132 can interact with the imaging-processing system 120. In certain embodiments, timing interface 126 may be adapted to communicate with a system interface 134 of the radiation therapy device 136 to determine timing of pulses of radiation from the source 112 and to control pulsed room lighting 138 to mitigate interference from room lighting during imaging of Cherenkov emissions and/or fluorescence by synchronizing lighting with image capture by cameras 102, 104, as discussed below with reference to FIG. 1B.

In certain embodiments of the systems of the present invention, for example as in the system 100 of FIG. 1A, the imaging system cameras 102, 104 are spectrally-sensitive cameras capable of providing spectral data permitting distinction between Cherenkov and fluorescent light, and some embodiments permitting distinction between light emitted by oxyhemoglobin and by deoxyhemoglobin.

In certain embodiments of the systems of the present invention, for example as in the system 100 of FIG. 1A, raw or de-noised images from the imaging system are recorded in one or more suitable digital memory systems (e.g., memory 122) as documentation of the radiation treatment.

In certain embodiments of the systems of the present invention, prior to each session for which monitoring of radiation delivery is desired, an enhancing and indicating agent is administered to the patient. In a particular example, the enhancing and indicating agent is a dose in the range of 20 milligrams per kilogram body weight of 5-delta-aminoievulinic acid (5-ALA), e.g., the dose being administered for an incubation time of approximately four hours before each divided radiotherapy session begins. In specific embodiments with a metabolically active tumor 110, some of the 5-ALA is metabolized to protoporphyrin IX (PpIX), which fluoresces when illuminated by Cherenkov light. PpIX production in normal tissue and tumor 110 is generally understood to be proportional to metabolic processes in those tissues; thus, a metabolically active tumor will tend to contain more PpIX and fluoresce more brightly. Other enhancing agents may be developed or utilized, and are contemplated as part of the present invention.

A. Direct Feedback Interface Control Units and Systems of the Invention

In certain advanced Cherenkov-based imaging systems of the present invention the system further provides direct feedback of the image information derived from capturing real-time Cherenkov radiation administration in order to instruct on the control of the beam source and/or beam shape. In certain embodiments, this is accomplished by means of incorporation of a direct feedback interface (DFI) control unit, wherein the DFI control unit is designed to provide direct/real-time communication between the camera and the radiation beam source unit and/or beam shaping unit (e.g., collimator), e.g., via a user display. Moreover, the Cherenkov-based feedback to the radiation beam source and/or beam shaping unit (e.g., to a LINAC), may be used by developers or service people to optimize the radiation beam source and/or beam shaping unit (e.g., LINAC performance).

As such, another embodiment of the present invention provides a direct feedback interface (DFI) control unit comprising a machine-readable medium having instructions stored thereon for execution by a processor to perform a method comprising the steps of:
  detection of Cherenkov radiation (and/or radiation emitted by fluorescent substances (fluorophores) excited by Cherenkov radiation) after exposure of a subject to high-energy radiation from a radiation beam source;
  creation of an image (e.g., image information);
  comparative analysis of the image to a reference image; and
  communication of the results of the comparative analysis to the radiation beam source unit, wherein such communication is capable of instructing modification of the beam profile (e.g., modification of beam shaping). In this way, the detected Cherenkov radiation may be used to directly control the linear accelerator, and the beam output. In certain embodiments, the image information may be stored on a second a machine-readable medium (e.g., wherein the second machine-readable medium is the machine-readable medium of the DFI control unit).

Another embodiment of the present invention provides an advanced Cherenkov-based imaging system comprising a direct feedback interface (DFI) control unit. In certain embodiments of the invention, a direct feedback interface (DFI) control unit may be incorporated into any system described herein. In certain embodiments, the present invention provides an advanced Cherenkov-based imaging system comprising:
  a radiation beam source (e.g., a particle accelerator or other device for providing high-energy radiation, which, for example, may be cross-sectionally shaped by a beam-shaping apparatus, e.g., a multi-leaf collimator);
  at least one camera capable of imaging Cherenkov radiation (and/or radiation emitted by fluorescent substances (fluorophores) excited by Cherenkov radiation);
  one or more processing units that enables the control of the radiation beam source; and
  a direct feedback interface (DFI) control unit,
  wherein the Cherenkov radiation is detected by the camera after exposure of a subject to high-energy radiation from the radiation beam source.

Alternatively, in certain embodiments, the direct feedback interface (DFI) control unit is implemented and integrated into an existing system via a supplemental kit, including for example, the direct feedback interface (DFI) control unit and any component of the system described herein not present in the existing system to which the kit will be added. Such kit is intended to form part of the present invention.

In certain embodiments of the present invention, a beam profile based on detected Cherenkov light or Cherenkov-stimulated fluorescence is directly fed back (e.g., in real time) to the radiation beam source unit or a designer, operator, or maintainer who is testing therapeutic radiation machine design, commissioning a newly installed therapeutic radiation machine, or performing periodic quality auditing and/or adjustment of a therapeutic radiation machine, or who wishes for any other purpose (e.g., treatment-plan verification) to characterize the spatial and temporal delivery of radiation by a therapeutic radiation machine to a treatment volume. In certain embodiments, a LINAC machine delivering radiation in the form high-energy electrons is described as an illustrative therapeutic radiation system, but no restriction is intended by this usage; all other radiation systems capable of inducing Cherenkov radiation in tissue are contemplated and within the scope of the invention.

FIG. 2 is a schematic depiction of portions of an illustrative system 200 for the coordinated observation and adjustment of a device providing radiotherapy based on direct feedback control. In certain embodiments of the invention, system 200 is equipped with a subsystem interface for determining beam profiles and dynamics by observation and analysis of Cherenkov radiation. For example, in certain embodiments, a beam-calibration phantom 202 is placed in a zone where it is desired to measure a profile of a radiation beam 108 provided by a radiation treatment machine 136. In particular embodiments, the zone may be a volume above or beside a treatment table (not depicted). In certain embodiments, the phantom 202 is a fluid-filled tank, the fluid in the tank being a translucent or transparent fluid having an index of refraction greater than that of air; in a particular embodiment, the fluid is water. In certain embodiments portions of the walls of the phantom 202 are transparent to Cherenkov light, e.g., the top and sides of phantom 202 consist largely of glass or transparent plastic. In a particular embodiment, the phantom 202 has sides constructed of acrylic sheets; another particular embodiment has sides constructed of polycarbonate panels. In a specific embodiment, a small amount of scattering agent and/or fluorophore is added to the liquid in the phantom 202 to enhance scatter of Cherenkov light without significantly affecting propagation of the radiation beam 108, overcoming the inherent directionality of Cherenkov light from a collimated radiation beam and allowing more light to be detected laterally around the phantom 202. The system 200 may also include an apparatus for preventing interference by room lighting or may be blacked out to prevent interference of ambient light with measurements of the Cherenkov radiation. However, room blackout for relatively long periods (e.g., a multi-image acquisition interval) is in general more feasible with a phantom 202 rather than a patient because live subjects may find blackout disturbing (e.g., claustrophobic) and workers cannot observe a patient's condition during blackout, which raises safety concerns.

In an alternative embodiment, the tank is filled with a transparent fluid such as silicone oil. In yet another embodiment, the phantom is formed from a high-index, transparent, material, such as a cast high-index plastic, e.g., plastic water or solid water (e.g., anthropomorphic), and may have both fluorophores and light-scattering additives embedded within it.

In certain embodiments of the present invention, the system 200 also includes one camera or a multiplicity of cameras; the illustrative embodiment of FIG. 2 includes two cameras 208, 210. For graphic simplicity the two cameras 208, 210 are depicted as being coplanar, but in certain embodiments, the cameras have lines of sight (e.g., line of sight 212 of camera 208) that are orthogonal to each other, e.g., in a plane that is orthogonal to the treatment beam 108. In certain embodiments, two orthogonal views suffice for the tomographic reconstruction of the three-dimensional light field intensity in the emission region 214 (cross-hatched region) from each simultaneously acquired pair of images from the cameras 208, 210. In particular embodiments, where only Cherenkov light is emitted from the emission region 214, the cameras 208, 210 may lie in a plane that is at angle θ with respect to the beam 108, where cos θ=c/(nv$_p$), c being the velocity of light in a vacuum, n the index of refraction of the material filling the phantom 202 (assumed herein for illustrative purposes to be homogeneous, but not necessarily so), and v$_p$ being the velocity of particles in the beam 108. In various other embodiments, a single camera is arranged to move to more than one position with respect to the phantom 202, or the phantom 202 is supported in a manner that permits its rotation with respect to one or more cameras, or some combination of one or more of these or other imaging arrangements is employed to obtain sufficient information for beam profile characterization (e.g., tomography). In certain embodiments where the beam 108 is known to have a radially symmetric spatial profile), a single camera may be used to fully characterize the spatial profile of the beam 108. Also in other embodiments, the particle beam source 112 and beam shaping subsystem 114 are attached to a gantry that enables them to move about a phantom 202 or a patient in the irradiation zone, delivering radiation to and from a range of angles.

The cameras 208, 210 are aimed to image at least part of the emission volume 214 and are coupled to a camera interface 118 of an image-processing system 120. (Camera connections to the camera interface 118 may be wired or wireless and are not depicted in FIG. 2 for clarity.) In certain embodiments, the camera interface 118 captures and stores digital images from the cameras 102, 104 in memory 122 for processing by at least one processor 124 of an image processing system 120. The processor 124 is capable of exchanging information not only with the camera interface 118 and memory 122 but with a timing interface 126, a display subsystem 128, and potentially other devices. The display subsystem 128 communicates with a user interface 130 through which a user 132 can interact with the imaging-processing system 120. Timing interface 126 is adapted to communicate with a system interface 134 of the radiation therapy device 136 to determine timing of pulses of radiation from the source 112 and potentially to control pulsed room lighting 138 to avoid interference from room lighting during imaging of Cherenkov emissions and/or fluorescence by synchronizing lighting.

In certain embodiments of the present invention, the phantom 202 is located within an environment that excludes significant amounts of daylight and light from other bright source such as room illuminators. In particular embodiments, the walls of the phantom 202 are coated on their interior surface with a light-absorbing coating except for camera viewing windows positioned in front of each camera, the coating being provided to absorb both stray light originating from outside the phantom 202 and to prevent emissions light from being reflected from the interior walls of the phantom 202 into a camera 208, 210.

In certain embodiments of the present invention, a beam source 112 (e.g., particle accelerator or other device for providing high-energy radiation) is aimed to provide a beam 108 of radiation through beam-shaping apparatus 114 to phantom 202. In a particular embodiment, the source 112 provides a beam of electrons having energy of 6 million electron volts (6 MeV) or greater; in a particular embodiment, the beam energy lies between 6 and 24 MeV. In an alternative embodiment, the source 112 produces a photon beam of 6 MeV or greater. In another alternative embodiment, the source 112 provides a proton or heavy charged particle beam. In yet another alternative embodiment, the source 112 produces a beam of electrons or photons having a substantial percentage of electrons or photons having energy of 1 MeV or greater. In the illustrative embodiment of FIG. 2, the radiation therapy machine 136 is a LINAC providing a beam of 6 MEV electrons.

Reference is now made to FIG. 1B, which schematically depicts the timing relationships of certain embodiments of the system 100 of FIG. 1 according to some methods of operation. In signal diagrams given in FIG. 1B and elsewhere herein, timing relationships are not necessarily drawn to scale: e.g., the width of a pulse may be exaggerated relative to the delay between pulses, or the duration (width) of a pulse depicted for one signal may not be proportional to that depicted for another signal. With emphasis on the sequence of events, i.e., which signals are On and which are Off at any given moment, Cherenkov radiation is emitted during high-energy radiation beam pulses 140; timing and intensity of Cherenkov emission closely correlates to timing and intensity of radiation pulses 140. Cherenkov-stimulated secondary light 142 emitted from naturally occurring, artificially administered, or drug-metabolite fluorescent materials can lag the radiation beam 140 and can decay exponentially after each pulse of the beam turns off, as illustrated. The time of this decay depends upon the emission lifetime of the biochemical species that was excited.

In one illustrative mode of operation, an effective Cherenkov shutter interval 144 that includes beam pulse 140 is used to image light primarily emitted by Cherenkov mechanisms, and an effective fluorescent shutter interval 146 is used to capture light emitted from the human subject or phantom by fluorescent and/or phosphorescent mechanisms. In this exemplary arrangement and mode of operation, room lighting 148 is pulsed Off for the duration of Cherenkov light emission (i.e., for duration of radiation pulse 140) and fluorescent emission 142 so that the relatively weak optical signals of interest may not be swamped by ambient light: in effect, the optical signal to noise ratio is improved by turning room lighting 148 off during emissions imaging. If the period of such pulses is significantly shorter than the flicker perception threshold of human vision, some dimming of room lighting relative to an unpulsed mode of operation may be visible, but no irritating flicker would be observed. In another exemplary mode of operation, room light is not pulsed, but an intensification step of image acquisition (not depicted) is gated On only during Cherenkov light emission, thus effectively rejecting most of the ambient light. In an example, during Cherenkov and/or fluorescent light acquisition, light imaged by cameras 102, 104 in FIG. 1A is recorded as pairs of consecutive images, with a first image of each pair recording of Cherenkov light emitted during beam pulse 140 and a second image of each pair recording light emitted during the fluorescent shutter interval 146. In certain embodiments, processor 124 of FIG. 1A executes machine-readable instructions in associated memory, such as memory 122, to reconstruct first (Cherenkov) tomographic image sets of the subject from the first images of all image pairs captured, to reconstruct second (fluorescence) tomographic image sets of the subject from the second images of all image pairs captured, and to produce an image set of fluorophore distribution in the subject based upon some mathematical relationships (e.g., ratio) between the first and second tomographic image sets. In various other, similar systems and/or modes of operation, non-tomographic imaging is performed, optionally enhanced by signal-processing steps such as background subtraction and median filtering to remove saturated pixels.

In modes of operation such as those where 5-ALA is administered, the fluorophore distribution is related to metabolic activity in the subject, and the tomographic image set of fluorophore distribution in the subject is indicative of metabolic activity throughout the imaged volume of the subject. The processor 124, or a processor of another computer device (not depicted), can further execute machine-readable instructions in memory 122 to compare the tomographic image set of fluorophore distribution in the subject against a tomographic image set of fluorophore distribution in the subject obtained during a prior radiation treatment session in order to produce a tomographic image set indicative of treatment effectiveness, i.e., changes (if any) in tumor metabolic activity.

In certain embodiments of system 100 an enclosure (not depicted herein) surrounds the subject and excludes ambient light from the subject, supporting the imaging of faint Cherenkov and fluorescence emissions. Additionally or alternatively, the coordinated functioning of timing interfaces 126 of system 100 (FIG. 1A) and pulsed room lighting 148 (FIG. 1B) serve to mitigate or prevent interference of ambient lighting with measurement of Cherenkov light and fluorescent light from an emission volume in the subject. The term "apparatus for preventing interference by room lighting" as used herein shall mean either or both of an enclosure surrounding and excluding ambient light from the subject, and the combination of timing interfaces 126 and pulsed room lighting 148.

In certain embodiments of the invention, Cherenkov radiation and/or associated fluorescent emissions, which are proxies for radiation deposition by high-energy photons and charged particles, may be employed in spatial (i.e., one-dimensional, two-dimensional, or three-dimensional) and temporal beam characterization or profiling. Herein, "temporal beam profiling" refers to the characterization of variations in beam intensity over time, whether during single pulses or averaged over portions of pulses or whole pulses, and "spatial beam profiling" refers to characterization of the distribution of beam intensity across the two-dimensional beam cross-section, or as a function of depth in a phantom or living subject, or both. The fullest possible profile of a beam pulse, which is acquired in various embodiments, consists of a three-dimensional spatial profile re-acquired at time intervals sufficiently frequent to capture all temporal beam behavior of interest for a given purpose: in effect, such data constitute a three-dimensional movie of pulse intensity, herein termed a four-dimensional beam profile. Herein, unmodified reference to a "beam profile" may denote a one-, two-, three-, or four-dimensional beam profiles.

The illustrative embodiment of FIG. 2 includes a LINAC user interface 214 that is capable of exchange information with a user 132. In certain embodiments, the information thus exchanged may include settings of control parameters for beam shaping system 114, particle beam source 112, movements of a gantry (not depicted) for directing the beam 108, and other measurable and/or controllable aspects of the therapeutic machine 136, whose readings or behaviors may in general be made known to the user 132 and modified by the user 132. In certain embodiments, the user 132 may, in several examples, be a designer monitoring the performance of a LINAC machine under development, a technician performing commissioning of a newly installed LINAC system, a technician performing periodic or scheduled quality auditing and/or adjustment of the LINAC system, a technician validating the delivery of a patient treatment plan using a phantom 202 prior to administration of the plan to a living subject, or a person who wishes for any other purpose to study and possibly adjust the temporal, spatial, and other characteristics of a beam 108 produced by therapeutic radiation system 136 in various modes of operation, and the interactions of such a beam with a phantom 202 and possibly with additional phantoms, living subjects (e.g., animal or human), or other targets.

In certain embodiments of the invention, Cherenkov-based imaging enabled by the imaging subsystem 120 supports visual, qualitative, and relative quantification characterization of profiles (one, two, three, or four-dimensional) of the beam 108, including such aspects as translations and rotations of the beam 108, shaping of the beam 108 by various settings of the beam-shaping subsystem 114, changes in particle energy (Cherenkov spectra and emission angles are both functions of particle energy, making such properties detectable in principle by the imaging subsystem 120), alterations in beam intensity (detectable because for a given particle energy, beam intensity and Cherenkov light brightness are proportional), and other aspects. Unlike methods used in the prior art for the characterization of beam profiles, the Cherenkov-based system 200 of FIG. 2 and other embodiments can acquire two- or three-dimensional beam profiles at rates limited only by the optical and other technical characteristics of the cameras (e.g., cameras 208, 210) and associated equipment (shutters, intensifiers, etc.): Cherenkov light (and/or fluorescent emissions stimulated by Cherenkov light) is intrinsically a continuous, high-resolution, four-dimensional source of information about radiation flux in the irradiated volume 214. Four-dimensional characterization of individual beam pulses is possible in various embodiments. Such data can be processed by the processor 124—e.g., in a tomographic manner, or using various model-based and other imaging approaches that will be familiar to persons versed in the art of medical image processing—to reveal features of interest in one, two, three, and four dimensions (e.g., derivative images and comparative images, delivered-dose maps) that are not available from existing technologies. In further examples, temporal performance of the therapeutic machine 136 can be assessed within a single pulse, or between pulses, or during the warm-up phase of operation of the LINAC. This information can be used by the operator 132 to adjust the performance of system 134. For example, the user 132 can issue commands to alter beam shaping by the beam-shaping subsystem 114. In another example, the user 132 or another person may make mechanical or electrical adjustments to the beam-generating mechanism of the source 112. In certain embodiments, all adjustable aspects of the operation of system 136 can be adjusted in a manner informed by the Cherenkov-derived information collected and processed by the image-display subsystem 120. In certain embodiments, such information may be transmitted to other computing and memory devices (not depicted) for post-processing, long-term storage, studies comparing different therapeutic machines or configurations, simulation, and other purposes. Advantageously, certain embodiments enable the rapid, high-resolution, four-dimensional characterization of radiation delivery to the phantom 202, without need to reposition the cameras 208 210 or the phantom 202, as well as adjustments of therapeutic machine 136 in a manner informed by such detailed and timely characterization.

Moreover, certain embodiments of the present invention enable efficient positioning of a phantom 202, or of other targets, with respect to the isocenter of the LINAC 136 (or other therapeutic radiation machine), in order that beam characterization or other tasks may be performed. In certain embodiments, the therapeutic radiation system indicates its isocenter location using intersecting visible lasers. In various embodiments of the invention, these lasers can be imaged by the same cameras (e.g., cameras 208 and 210) that are used to image Cherenkov and/or fluorescent light. Software control and feedback as described herein (e.g., through the system interface 134 and imaging subsystem 120) provide isocenter alignment information to the user 132. In a particular example, isocenter alignment laser images may be compared to physical or virtual registration marks on the phantom 202 as imaged to the user 132, and the phantom's position is adjusted accordingly: for example, control of platform positioning of the system 136 is conducted through the system interface 134, either manually by the user 132 or as determined by software computed by the imaging subsystem 120 or another computing device, to produce satisfactory alignment of isocenter of the phantom 202 or a region or target therein. Such embodiments minimize the time required for phantom setup and offer, for example, advantageous time savings for quality audit processes compared to lower-resolution electronic beam-locating systems. Because the camera or cameras of various embodiments have relatively very high spatial resolution and can be dual-used for both laser observation and Cherenkov observation, embodiments have a flexibility of set-up which exceeds that of known electronic diode or ionization chamber ionization processes.

In certain embodiments, the user interfaces 130 and 214 are supplemented or replaced by direct informatic communications interfaces and the human user 132 is supplemented or replaced by a computational system, such as a software program or artificial intelligence, that is configured to exchange information with image-processing subsystem 120, with the system interface of the therapeutic machine 136, and potentially with other measuring devices, mechanical systems, computing devices, and other devices or systems. In such embodiments, the software program or artificial intelligence performs some or all of the functions of evaluation, comparison, and adjustment that in the embodiment of FIG. 2 are performed by the human user 132.

In certain embodiments the operation of system of the present invention, and as illustrated by the flowchart of method 300 of FIG. 3, adjustment of the therapeutic system 136 is performed to produce a beam of desired characteristics within a specified accuracy range. In a preliminary positioning step 302 that may entail imaging of the system isocenter, the phantom 202 may be positioned within the treatment space of the system 136 so that the center of the phantom 202, or some other point within the phantom 202, is located at the system isocenter. In a beam-programming or adjustment step 304, the system 136 may be set to produce a beam 108 of a given character for irradiation of the phantom 202: such characteristics as intensity, pulse duration, pulse frequency, number of pulses, and two-dimensional beam profile as determined by the beam-shaping subsystem 114, among other characteristics, may be set to predetermined values. The predetermined values may be specified to serve a manufacturer's test plan, or as part of a patient treatment plan, or according to other criteria. In an irradiation step 306, one or more pulses of radiation are supplied by the therapeutic system 136, while imaging (e.g., stereoscopic gated imaging) of the Cherenkov light and/or secondary fluorescent light induced in the phantom by the radiation is performed. In an image-processing or beam-profile calculation step 308, data from the cameras 208, 210 is processed by the imaging subsystem 120 to produce, in this illustrative method, a two-dimensional irradiation pattern or beam profile at the system isocenter. In a display and comparison step 310, an expected profile and the observed profile are compared. Such comparison may be visual and ad hoc, or quantitative, or may combine several modes of comparison: in any case, such comparison produces a judgement, whether ad hoc or numerical, as to whether the expected irradiation pattern is sufficiently similar to the observed radiation pattern or not. If it is sufficiently similar, then the method may proceed to the testing 316 of another configuration of the system 136 or may terminate. If agreement between expected and observed radiation is unsatisfactory, then an adjustment step 312 is performed, in which one or more adjustable aspects of the mechanism and/or operation of the system 136 is performed by one or more of the operator 132, software, or an additional person. In a looping or convergence phase 314, irradiation and observation 306, beam profile calculation 308, comparison 310, and possibly adjustment 312, as described above, are repeated until satisfactory agreement between expected and observed radiation delivery is observed, a different system configuration is set up for testing 316, or the operator elects to end the procedure 318.

The calibration method 300 is illustrative of a broad class of procedures and methods by which the system 200 or various other embodiments may be operated. The systems and methods of most embodiments entail rapid and information-rich feedback to characteristics of the therapeutic system 136 based on observed and processed Cherenkov light or secondary fluorescence induced in the phantom 202 by the radiation beam 108. All methods of operation of system 200 and various other embodiments, including those not explicitly described herein, are contemplated and within the scope of the invention.

B. Enhanced Beam Characterization: Integration of Cherenkov and Non-Cherenkov Sensing Another embodiment of the present invention provides high resolution dose quantified Cherenkov-based images, through enhanced beam characterization. In particular, certain embodiments of the present invention address the challenges of fast 3D dosimetry utilizing a technique that allows for real-time dose imaging, e.g., in water phantoms. While known non-Cherenkov radiation measurement devices, such as external portal imaging devices (EPID), can provide a 2D transverse distribution of a transmitted beam, and the Cherenkov imaging provides an accurate lateral view of the dose; the tools and methods of the present invention provide the integration of these measures, e.g., providing for the simultaneous acquisition of EPID images and lateral Cherenkov images. In certain embodiments, the integration of these measures produces a consistent 3D distribution of the deposited dose. In particular embodiments the non-Cherenkov radiation measurement device, e.g., EPID, and the Cherenkov techniques provide images with high frame rates (~10 fps) which permits real-time 3D beam reconstruction. As such, and in particular embodiments, this affords the ability to perform pre-treatment plan verification and quality assurance due to the high spatial and temporal resolution of the measured 3D dose distributions produced.

Traditionally, measurement methods for therapeutic radiation beams have depended on radiographic or Gafchromic film dosimetry for obtaining planar two-dimensional (2D) dose distributions inside a dosimetry phantom placed inside the treatment zone. Although film dosimetry is high-resolution, the process is cumbersome, not real-time, and may exhibit processing-dependent variability. Other known techniques include electronic portal imaging devices (EPIDs), ionization chamber arrays, and semiconductor arrays. For example, Theraview Technology's EPID images over a 40×40 cm square planar array with 1024×1024 pixels and 12-bit acquisition. A digital analogue to film dosimetry, EPID imaging is easy to use—EPIDs can be integrated with therapeutic systems and software-controlled—but the true experimental measurement may only be made at a single planar slice: thus, for EPIDs and other planar-type dosimetry methods, fully three-dimensional beam characterization is difficult and time-consuming to perform or may be impossible, while beam characterization in 3D over time (herein referred to as "four-dimensional" characterization) is extremely difficult and rarely, if ever, performed. Also, planar array-based systems have inherently limited resolution due to the finite spacing of the detectors.

Additional dosimetry methods currently under development include gel and plastic or liquid scintillation dosimetry. Despite several advantages, gel dosimetry is time consuming and requires post-processing and a readout mechanism such as optical computed tomography or magnetic resonance imaging, while scintillation methods require careful calibration and suppression of the stem effect. Finally, none of the currently known techniques are truly water equivalent, as the active medium is not water itself, which is of particular importance, as water is the gold-standard dosimetry medium due to its radiological close equivalence to tissue, cheap abundance, high purity, and ease of interinstitution standardization.

As such, another embodiment of the present invention provides a quantifier integration (QI) unit comprising a machine-readable medium having instructions stored thereon for execution by a processor to perform a method comprising the steps of:
- detection of Cherenkov radiation (and/or radiation emitted by fluorescent substances (fluorophores) excited by Cherenkov radiation) after exposure of a subject to high-energy radiation from a radiation beam source, and establishment of a Cherenkov radiation image (e.g., image information);
- detection of non-Cherenkov radiation after exposure of a subject to high-energy radiation from a radiation beam source, and establishment of a non-Cherenkov radiation measurement; and
- integration of the non-Cherenkov (i.e., quantitative) radiation measurements (e.g., from an ionization chamber or an EPID) with the Cherenkov radiation image (e.g., tomography), to produce a quantitatively calibrated high resolution Cherenkov image. The language "high resolution" as used herein describes high spatial and temporal resolution of the measured dose distribution, e.g., three-dimensional dose distribution. The quantitatively calibrated Cherenkov images represent beam geometry and intensity that are labeled with absolute dose units. These images may be used to establish a calibration where a given intensity of Cherenkov light at a given point of the phantom is experimentally associated with a particular intensity of ionization radiation in absolute dose units as measured by, for example, an EPID or ionization chamber. Further, in particular embodiments, non-Cherenkov radiation measurements (such as ionization chamber measurements) at sampling of discrete locations within the phantom or treatment volume (e.g., along the beam axis) can be used to produce a table or map (one-, two-, or three-dimensional) of local conversion factors that link units of observed Cherenkov brightness to absolute dose units in different portions of a beam.

In certain embodiments of the quantifier integration (QI) unit of the present invention, the non-Cherenkov radiation measurement device is selected from the group consisting of an ionization chamber, EPID, diodes, and any combination thereof. In certain embodiments, the method may further comprise the step of communication of the quantitatively calibrated high resolution Cherenkov image to the radiation beam source unit. In this way, in certain embodiments, the detected Cherenkov radiation may be used to directly control the linear accelerator, and the beam output. In certain embodiments, the quantitatively calibrated high resolution Cherenkov image may be stored on a second a machine-readable medium (e.g., wherein the second machine-readable medium is the machine-readable medium of a DFI control unit). In certain embodiments, the non-Cherenkov radiation measurements allow quantitative estimation of the depth-vs.-dose curve from the Cherenkov radiation image.

Another embodiment of the present invention provides an advanced Cherenkov-based imaging system comprising a quantifier integration unit. In certain embodiments of the invention, a quantifier integration (QI) unit may be incorporated into any system described herein. In certain embodiments, the present invention provides an advanced Cherenkov-based imaging system comprising:

- a radiation beam source (e.g., a particle accelerator or other device for providing high-energy radiation, which, for example, may be cross-sectionally shaped by a beam-shaping apparatus, e.g., a multi-leaf collimator);
- at least one camera capable of imaging Cherenkov radiation (and/or radiation emitted by fluorescent substances (fluorophores) excited by Cherenkov radiation);
- one or more processing units that enables the control of the radiation beam source;
- a non-Cherenkov radiation measurement device; and
- a quantifier integration unit,
- wherein the Cherenkov radiation is detected by the camera and non-Cherenkov radiation is detected by the non-Cherenkov radiation measurement device after exposure of a subject to high-energy radiation from the radiation beam source.

Alternatively, in certain embodiments, the quantifier integration unit is implemented and integrated into an existing system via a supplemental kit, including for example, the quantifier integration unit and any component of the system described herein not present in the existing system to which the kit will be added. Such kit is intended to form part of the present invention.

Figure 4A:
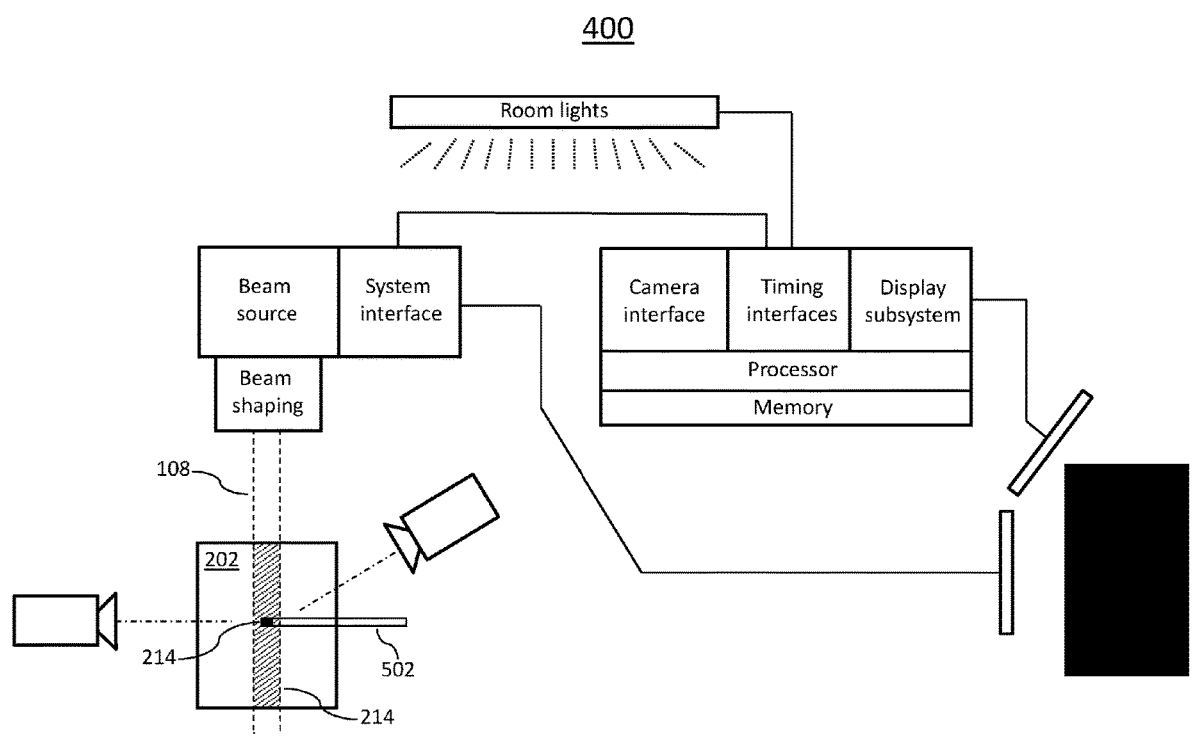
FIG. 4A is a schematic block diagram of an apparatus for the calibration of Cherenkov observations to in situ, high-accuracy radiation measurements in a therapeutic radiation system and phantom.

Reference is now made to FIG. 4A, which schematically depicts portions of an illustrative system 400 according to certain embodiments of the invention. System 400 resembles system 200 of FIG. 4A but with the addition of a non-Cherenkov radiation measurement device 402. In certain embodiments, the non-Cherenkov radiation measurement device is an ionization chamber. For example, a typical ionization chamber is a gas-filled chamber in which high-energy (ionizing) radiation creates free charges that can be detected and whose rate of appearance corresponds to the intensity of high-energy radiation within the ionization chamber. The term "ionization chamber" is often applied to denote entire radiation-probe systems that include an ionization chamber, not only to the chamber per se. Ionization chamber probes are generally considered the gold standard for calibration of therapeutic radiation systems because they give a precise and highly localized measure of the ionizing radiation delivered by a therapeutic system at a given point, e.g., a point within a water-filled phantom. In particular embodiments, the ionization chamber is the cylindrical, waterproof Farmer-type ion ionization chamber, which is recommended by various dosimetry protocols for dose measurement of radiotherapy beams. The chambers of such probes typically have volumes of 0.6-0.65 cm$^3$ and can report measured calibrated exposure accurate to National Institute of Standards & Technology (NIST) certified standards, which can be directly mapped to dose delivery at that point. The value of having one or more measures of exposure or dose allows calibration of the Cherenkov intensity into similar intensity units.

In certain embodiments of the present invention, measurements from ionization chamber are combined/integrated with Cherenkov imaging (e.g., tomography) in order to produce accurately calibrated Cherenkov images or non-image measurements. In certain embodiments, a localized, highly precise measurement of radiation intensity is obtained by an ionization chamber at a given point (e.g., a point inside a water-filled phantom), the ionization chamber is removed, and the intensity of Cherenkov light emitted under identical radiation conditions by the sub-volume of the phantom corresponding to that previously occupied by the ionization chamber is observed. (This order of events may be varied; e.g., Cherenkov imaging may precede ionization chamber measurement.) A calibration is thus enabled by which a given intensity of Cherenkov light at a given point of the phantom is experimentally associated with a particular intensity of ionization radiation as measured by ionization chamber in absolute dose units. Ionization chamber measurements at sampling of discrete locations within the phantom or treatment volume (e.g., along the beam axis) can be used to produce a table or map (one-, two-, or three-dimensional) of local conversion factors that link units of observed Cherenkov brightness to absolute dose units in different portions of a beam. In an example, the resulting mapping of units is depth-dependent; in another example, the mapping is dependent on depth and on radial distance from beam center; in another example, the mapping is dependent on depth, radial distance from beam center, and distance from beam center. Thus, in certain embodiments, the tools and methods of the present invention enable the production of Cherenkov images of beam geometry and intensity that are labeled with absolute dose units, not merely with units of optical brightness.

In certain embodiments, for example in the illustrative system 400 of FIG. 4A, the non-Cherenkov radiation detection device 402 is a Farmer-type ionization probe inserted into the liquid-filled phantom 202. The actual gas chamber 404 of the probe 402 is at one tip of the probe 402. In particular embodiments, the volume of the chamber 404 is presumed to be sufficiently small relative to the irradiated volume 214 to permit meaningfully localized characterization of beam 108 intensity.

Figure 4B:
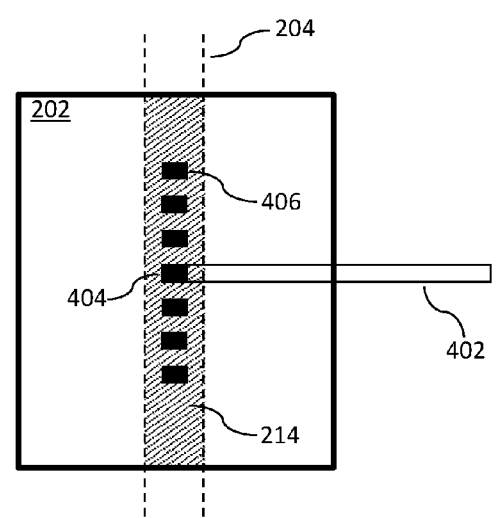
FIG. 4B is a more detailed view of portions of the system of FIG. 4A.

FIG. 4B depicts a closer view of one embodiment of the phantom 202 and probe 402, omitting cameras and other apparatus for clarity. In one illustrative method of operation of the system 400, the probe 402 may be moved so that the ion chamber 404 occupies a series of positions along the axis of the beam 108. In FIG. 4B, these points (e.g., position 406) are depicted as evenly spaced along a line and seven in number, but in general need not be evenly spaced and may be of any number or spatial arrangement. In certain methods of operation, either the entire phantom 202 may be moved along the axis of the beam 108 or the location of the chamber 404 may be moved. For clarity, only positions of the chamber 404, not the whole probe 402, are depicted in FIG. 4B.

In certain embodiments of the present invention, and in the illustrative method partly illustrated in FIG. 4B, ionization chamber measurements of radiation intensity are made centrally along the axis of beam 108. In certain embodiments, after all measurements, the probe 402 is removed from the phantom 202 and one or more Cherenkov images (i.e., images of Cherenkov light or secondarily emitted fluorescent light) of the irradiation volume 214 are acquired. The average intensity of the observed light from within each of the seven measurement volumes is then directly correlated with radiation intensity as measured by ionization chamber. In one example, a continuous one-dimensional calibrative function can be calculated (e.g., by interpolation) from the discretely measured correspondences of radiation intensity to light intensity and applied to subsequent Cherenkov images of the phantom in order to accurately associate radiation intensity units with light-intensity units. In certain other methods of operation, radiation intensity measurements may be made within the irradiation volume 214 according to various geometric schemes other than or addition to that depicted in FIG. 4B (e.g., measurements may be located so as to sample a planar cross-section, or more than one planar cross-section, or a given sub-volume of the irradiation volume 214, or multiple one-dimensional transects similar to that depicted in FIG. 4B).

Certain embodiments of the present invention advantageously combine the features of ionization chambers or other high-precision radiation tools with those of Cherenkov imaging. Ionization chamber dose measurements are highly accurate but slow and typically not acquired in more than one dimension (e.g., along beam axis for depth versus dose curves, or orthogonally to beam axis for beam profile measurements) at a time. In comparison, Cherenkov imaging has the inherent strengths of rapidity and provision of two-, three-, and four-dimensional data very quickly. Cherenkov imaging does, however, require calibration for quantitative accuracy of dose estimation. Using the tools and methods described herein, combining the two types of measurements—i.e., high-accuracy point or small-volume dose measurements and Cherenkov imaging—is capable of exploiting the strengths of both modalities while mitigating their weaknesses.

Figure 5:
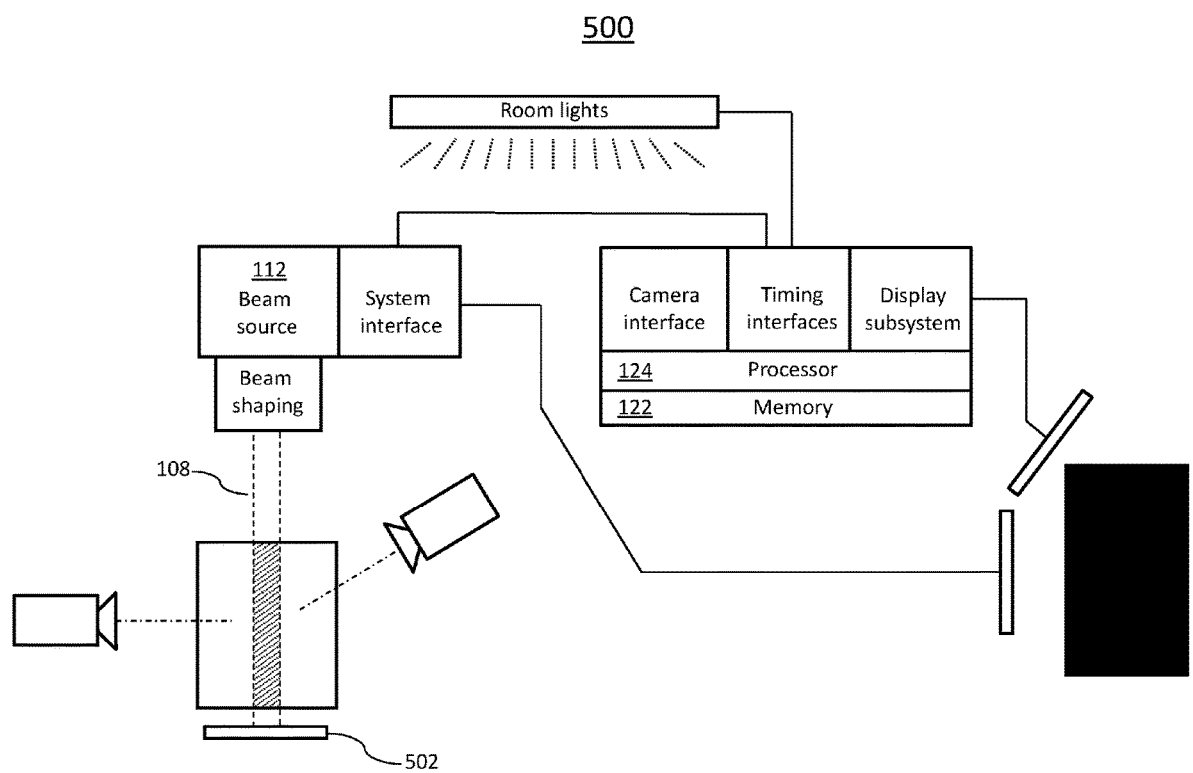
FIG. 5 is a schematic block diagram of an apparatus for coordinated Cherenkov and non-Cherenkov observation high-energy beam profiles in a therapeutic radiation system.

Reference is now made to FIG. 5, which schematically depicts portions of an illustrative system 500 according to certain embodiments of the invention. System 500 resembles system 200 of FIG. 2 but with the addition of a non-Cherenkov radiation measurement device 502. In one example, the imaging device 502 is an external portal imaging device (EPID). One type of EPID consists essentially of a converter layer that converts incident radiation into light and a two-dimensional array of electronic sensors capable of sensing the light thus produced. In certain embodiments, the converter layer may consist essentially of some form of metal plate in contact with either an ionization medium or a phosphor screen. Further, in certain embodiments, the detection array may be in a camera trained upon the converter, or in extended solid-state array (active matrix flat panel) parallel and close to the converter. In some EPID technologies, conversion is omitted in favor of direct detection by active matrix flat-panel devices. In essence, an EPID serves as a piece of electronic film whose image may be retrieved, in the form of digital data, at relatively high speed and without the need for development.

Regardless of technological basis, a typical EPID is capable of imaging a rectangular two-dimensional cross-section of the beam 108 (typically orthogonal to the beam 108) at a given distance from the source 112. In one illustrative system 500, data from the EPID may be routed to the memory 122 and processor 124 of the Cherenkov imaging system 120, e.g., via a quantifier integration unit described herein; in certain alternative embodiments, EPID data may be separately processed through a different interface, memory, and processing system (not depicted), such as is already provided in an integral manner with some LINAC or other therapeutic-radiation systems, before being routed to or integrated with the Cherenkov imaging subsystem 120. Provisions for mounting, moving, and communicating with the EPID are for simplicity omitted from FIG. 5, but the nature of such provisions will be familiar to persons versed in the construction of such devices, in light of the disclosure of the present invention.

Certain embodiments of the present invention employ one or more non-Cherenkov measurement devices, which may employ one or more sensing modalities (e.g., ionization, direct-detection flat panel), to acquire beam information. In one example, the EPID of FIG. 5 acquires lateral beam information, i.e., one- or two-dimensional radiation intensity information in the plane of the non-Cherenkov device, which is orthogonal to the beam 108. In addition to non-Cherenkov dose information, Cherenkov emission information is acquired from one or more viewpoints, e.g., by a moving camera, or a camera fixed relative to a moving irradiation target, or by a multiplicity of cameras. Thus, in certain embodiments, information on delivered dose is obtained from a plurality of viewpoints using at least two distinct sensing modalities, one of which is Cherenkov imaging. In one example, the lateral profile or extent of the beam at the back of the treatment area (i.e., in the position of the EPID 502 depicted in FIG. 5) can be measured and, with assumptions based on lateral beam divergence and penumbra, estimates of the three-dimensional image of beam 108 can be made. This information, combined with axial decay of the signal from lateral Cherenkov imaging, can be used to estimate full four-dimensional dosimetry in a water tank or other phantom.

Advantageously, the present invention enables measurements to be made in real time, allowing characterization of phantom-delivered complex treatment plans at all points in the treatment. This can be a valuable tool for routine patient plan verification prior to delivery in the patient; verification could be performed on each plan prior to delivery. This is especially important for complex treatment plans, where verification is not only necessary but is reimbursed by some systems of health-care funding (e.g., by Medicare in the US, as "pretreatment simulation").

In addition, in certain embodiments of the present invention, the EPID or other non-Cherenkov imaging information can be combined with Cherenkov imaging acquired during actual patient irradiation. Although Cherenkov light cannot typically be detected from deep within human tissue, surficial Cherenkov light may be imaged as a proxy for skin dose. In effect, Cherenkov light emitted at or just below the skin surface upon beam entry serves as a cross-sectional (through the generally non-planar skin surface) image of the incident beam, conveying information both on intensity profile and overall geometry: this information can be combined with beam profile data transmitted through the medium and detected by EPID or other non-Cherenkov information using a variety of mathematical modeling procedures to produce estimates of internal patient dose geometry, and in certain embodiments, with high temporal resolution, that are more accurate than those achievable from either Cherenkov or non-Cherenkov sensing alone. It is advantageous for patient safety and treatment efficacy to have improved knowledge of internal dosage geometry.

C. Temporal and Spectral Light Management

Given current limitations on measuring Cherenkov radiation, typically accomplished by known temporal gating techniques to subtract room lighting/illumination from such measurements, the dynamic range of measurements has been substantially reduced. However, the temporal and/or spectral illumination management features of the present invention may serve as a dynamic range extender for these measurements.

In one embodiment, temporal control sequences may be used for improved image capture. As such, another embodiment of the present invention provides a speed gating unit employing a temporal control sequence comprising a machine-readable medium having instructions stored thereon for execution by a processor to perform a method comprising the steps of:

controlling the temporal sequence gating of lighting in a room; and
controlling the temporal sequence gating of the exposure of at least one camera capable of imaging Cherenkov radiation upon exposure of a subject to high-energy radiation from the radiation beam source,
such that the gating of lighting and the camera exposure are pulsed at millisecond speed.

Another embodiment of the present invention provides an advanced Cherenkov-based imaging system comprising a speed gating unit employing a temporal control sequence. In certain embodiments of the invention, a speed gating unit employing a temporal control sequence may be incorporated into any system described herein. In certain embodiments, the present invention provides an advanced Cherenkov-based imaging system comprising:

a radiation beam source (e.g., a particle accelerator or other device for providing high-energy radiation, which, for example, may be cross-sectionally shaped by a beam-shaping apparatus, e.g., a multi-leaf collimator);
at least one camera capable of imaging Cherenkov radiation (and/or radiation emitted by fluorescent substances (fluorophores) excited by Cherenkov radiation);
one or more processing units that enables the control of the radiation beam source;
one or more illumination devices for use in room lighting; and
a speed gating unit employing a temporal control sequence designed to complimentarily control the temporal sequence gating of the room lighting and the camera exposure, wherein the speed gating of each is pulsed at millisecond speed, wherein the Cherenkov radiation is detected by the camera after exposure of a subject to high-energy radiation from the radiation beam source. In certain embodiments of the present invention, the system may operate without the use of an intensifier, e.g., an intensifier free system for measuring Cherenkov radiation.

Alternatively, in certain embodiments, the speed gating unit employing a temporal control sequence is implemented and integrated into an existing system via a supplemental kit, including for example, the speed gating unit employing a temporal control sequence and any component of the system described herein not present in the existing system to which the kit will be added. Such kit is intended to form part of the present invention.

Reference is now made to embodiments of the invention that use spectral and/or temporal selectivity with regard to the provision of ambient light, and to the admission of ambient and/or Cherenkov or secondary luminescent light to imaging systems. Because Cherenkov and secondary fluorescent light are primarily in the visible spectrum, room lighting and other ambient light sources compete in the detectors (e.g., Cherenkov imaging cameras) with Cherenkov and fluorescent light to be imaged. Typically, the undamped ambient light signal outweighs the light signal of interest by several orders of magnitude. Thus, pulse-width-scale time management of illumination and/or light sensing have previously been employed to enhance detection of the signal of interest: that is, to reduce or eliminate ambient light for short intervals of time (e.g., during a radiation pulse) with coordinated sensing of the signal of interest (e.g., gating of intensifier). A form of such time management of illumination and sensing is discussed hereinabove with reference to FIGS. 1A and 1B.

Figure 6A:
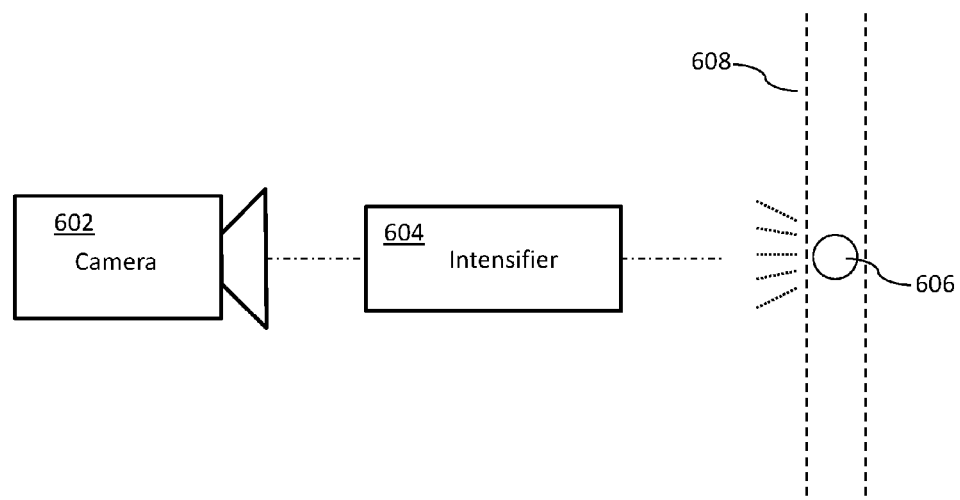
FIG. 6A is a schematic block diagram of a camera system for observing Cherenkov radiation consisting of both an image intensifier and a camera.
Figure 6B:
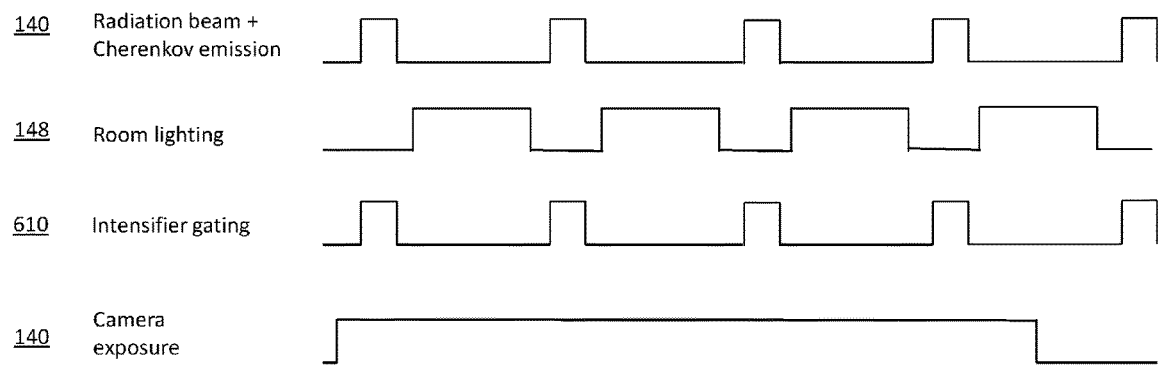
FIG. 6B is a diagram showing the approximate timing relationships of portions of the system of FIG. 6A in one mode of operation.

To clarify, FIG. 6A schematically depicts portions of an illustrative Cherenkov imaging system according to one known form. Included are a camera 602, an intensifier 604, and a source of Cherenkov light 606 stimulated by a radiation beam 608. Illustrative timing relationships for these components are depicted in FIG. 6B. Pulses of radiation 140 (and thus of Cherenkov light) are typically on the order of 3 μsec duration; gaps between pulses are typically from several μsec to several tens of milliseconds duration. In particular embodiments, room lighting 148 is gated Off in sync with radiation/Cherenkov pulses 140, as depicted in FIG. 6B; however microsecond-speed dimming or quenching of light sources (even LEDs) at the power levels of area lighting is not generally practical, or if possible requires specialized (and therefore costly) light sources. In practice, while the room lights are gated Off (and may in fact be only dimmed, due to response lag), the intensifier 604 of FIG. 6A is gated On (signal 610 of FIG. 6B) in sync with radiation and Cherenkov light 140. Further, the camera 602 of FIG. 6A exposes an image for a number of pulses, each of which is synchronously intensified. In effect, the camera 602 integrates or sums the intensifier output over some number of pulses; in FIG. 6B, the number of pulses summed is four, but the number summed can vary from 1 to any number (e.g., 100 or 1000).

Figure 6C:
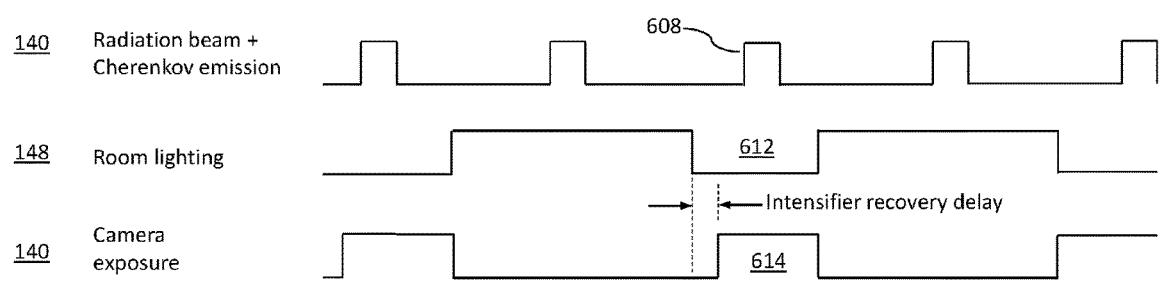
FIG. 6C is a diagram showing the approximate timing relationships of portions of a Cherenkov therapeutic radiation imaging system according to an embodiment of the invention.

The foregoing scheme may be useful but has the disadvantage that microsecond-speed intensifier gating is required. Leaving the intensifier gated open for longer periods, except in darkness, has a strong tendency to saturate the intensifier. While microsecond gating may be practical in certain situations, in general it is costly. The present invention, therefore, provides in certain embodiments, temporal control sequences that have been identified herein, which are designed to complimentarily control the temporal sequence gating of the room lighting and the camera exposure, such that speed gating of each is pulsed at millisecond speed. As depicted in FIG. 6C, room lighting 148 may be dimmed for intervals surrounding selected pulses 140 (in this example, every other pulse; in general, every nth pulse, where n may range from 1 to any higher integer). Each interval for which the room lighting is dimmed may be arbitrarily long, but in certain embodiments is short enough, and recurs at a long enough interval, so that the human eye perceives no flicker as a consequence. Moreover, camera exposure 140 is On during the Off period of the room lighting 148. Complementary pulsing of room lighting 148 and camera exposure 140 occurs, in certain embodiments, at millisecond speed rather than at microsecond speed, obviating the need for more costly millisecond gating (e.g., of the intensifier 604). Also in certain embodiments, the intensifier 604 is not gated but is rather permitted to saturate during room-light On intervals; after commencement of a room-light Off interval (e.g., interval 612), a delay permits the intensifier to desaturate before the camera exposure interval 614 begins. In certain other embodiments, the intensifier is gated but at millisecond speeds rather than microsecond speeds as in FIG. 1B and FIG. 6B. Variations of the timing relationships in FIG. 6C not depicted or discussed herein are contemplated and within the scope of the invention described herein; the representation of FIG. 6C is in no way intended to be restrictive.

In certain embodiments of the present invention, the present invention provides spectral forms of illumination management, additionally or alternatively to temporal forms of illumination management as described hereinabove. Spectral illumination management for Cherenkov imaging is based on the fact that primary (unfiltered) Cherenkov light, though partly visible, has a spectrum (given by the Frank-Tamm formula) that is distinct from that of typical illumination in a room, with more energy in the green, blue, and ultraviolet portion of the spectrum. In one illustrative embodiment, ambient illumination is filtered in a manner approximately complementary or inverse to the Cherenkov spectrum of light produced by a water phantom: thus, during the emission and imaging of Cherenkov light, an intensifier and camera will receive as inputs primarily Cherenkov emissions, not ambient emissions. For example, ambient illumination may be passed through a low-pass filter with a cut-off wavelength of approximately 600 nm (thus excluding green, blue, and violet). In another example, light sources (e.g., LEDs) emitting light that is substantially limited to wavelengths longer than approximately 600 nm are employed for illumination, obviating the need for filtering or increasing the efficacy of filtering; such LEDs may supply continuous room illumination, or may be turned On (or left On) while broader-spectrum LEDs are gated Off, either for entire imaging sessions or for brief (e.g., gated) intervals. In another embodiment, complementary filtration of light is performed at the optical input of an intensifier, so that the intensifier only "sees" Cherenkov light. For example, in certain embodiments, light entering an intensifier may be passed through a high-pass filter with a cut-on wavelength of approximately 600 nm (thus passing green, blue, and violet) when imaging a water tank, or pass through a cut-off filter passing red and NIR light when imaging a patient. Some embodiments include filtration of both illumination and intensifier/camera input. In a specific embodiment, the present invention contemplates a sufficiently sensitive camera, as for example with a cooled charge-coupled device sensing array, which would not need an intensifier; systems including such devices are within the scope of the invention.

Similar considerations apply in certain embodiments to enhanced detection of Cherenkov-stimulated fluorescence, whose detection may also be enhanced by suppressing ambient light and/or light admitted to an imaging system in a manner that is spectrally complementary to the light or makes use of the relationships between spectrum and direction of light travel which are specific to the room lights and Cherenkov emission.

Of note, the spectrum of Cherenkov light actually observed may reflect the filtering effects of media such as tissue. For example, Cherenkov light passing through tissue is significantly red-shifted, having lost most of the UV, blue and green light to absorption. This results in a spectrum with more energy in the red and near-infrared portions of the spectrum than in the blue and violet portions of the spectrum. Thus, in certain embodiments, spectral specifics of illumination and filtering may be adapted to the spectral character of the particular Cherenkov light to be imaged.

Thus, certain embodiments of the present invention include temporal and/or spectral illumination management features which negate or mitigate the need for time gated Cherenkov imaging. Existing implementations of Cherenkov imaging are time gated, with the pulses of the linear accelerator delivering the radiation in 3 to 4 microsecond bursts and detection of Cherenkov and/or luminescent emissions gated to these bursts. Such time gating reduces room-light interference with the signal of interest, but entails more costly electronics needed to gate the intensifier. If imaging can be done without a gated intensifier, camera costs can be substantially less, and continuous wave imaging can be achieved with intensification technologies, e.g., such as those used for standard night-vision imaging. Also, in certain embodiments gating and spectral modulation of illumination are hybridized so that room lights are temporally dimmed or wavelength filtered to minimize the ambient light signal picked up with the Cherenkov signal, and a lower cost-camera is used for imaging. In certain embodiments, system designs could be implemented (e.g., originally or via a supplemental kit) that substantially reduces Cherenkov camera cost in tradeoff for modest cost lighting system changes.

III. Methods of Cherenkov-Based Imaging

The present invention provides certain methods that are useful in the systems and tools of the present invention, however, these methods are intended separately to be part of the inventive concept of the present invention.

Such methods include, methods of measuring Cherenkov radiation using direct feedback control of the radiation beam source, quantitatively calibrating Cherenkov images, and through temporal control sequences.

In a particular embodiment, the present invention provides a method of measuring Cherenkov radiation with direct feedback control comprising the steps of:
  detection of Cherenkov radiation after exposure of a subject to high-energy radiation from a radiation beam source; creation of an image;
  comparative analysis of the image to a reference image; and communication of the results of the comparative analysis to the radiation beam source unit, wherein such communication is capable of instructing modification of the beam profile.

In another particular embodiment, the present invention provides a method of measuring Cherenkov radiation to quantitatively calibrate Cherenkov images comprising the steps of:
  detection of Cherenkov radiation after exposure of a subject to high-energy radiation from a radiation beam source, and establishment of a Cherenkov radiation image;
  detection of non-Cherenkov radiation after exposure of a subject to high-energy radiation from a radiation beam source, and establishment of a non-Cherenkov radiation measurement; and
  integration of the non-Cherenkov radiation measurements with the Cherenkov radiation image, to produce a quantitatively calibrated high resolution Cherenkov image.

In another particular embodiment, the present invention provides a method of measuring Cherenkov radiation through temporal control sequences comprising the steps of:
  controlling the temporal sequence gating of lighting in a room; and
  controlling the temporal sequence gating of the exposure of at least one camera capable of imaging Cherenkov radiation upon exposure of a subject to high-energy radiation from the radiation beam source, such that the gating of lighting and the camera exposure are pulsed at millisecond speed.

INCORPORATION BY REFERENCE

The entire contents of all patents, published patent applications and other references cited herein are hereby expressly incorporated herein in their entireties by reference. In particular, the entire contents of PCT Patent Application Serial No. PCT|US14/66668 filed Nov. 20, 2014; PCT Patent Application Serial No. PCT|US12/38609 filed May 18, 2012; and U.S. Patent Application US 2014/0114150 A1, are hereby incorporated herein by reference.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. A direct feedback interface (DFI) control unit comprising a machine-readable medium having instructions stored thereon for execution by a processor to perform a method comprising the steps of:

detection of Cherenkov radiation after exposure of a subject to high-energy radiation from a radiation beam source;

creation of an image;

comparative analysis of the image to a reference image;

direct communication of the results of the comparative analysis to a radiation beam source unit or a beam shaping unit, wherein such communication is direct feedback capable of instructing real-time modification of the beam profile.

2. The DFI control unit of claim 1, wherein the modification of the beam profile is modification of beam shaping.

3. An advanced Cherenkov-based imaging system comprising:

a radiation beam source;

at least one camera capable of imaging Cherenkov radiation;

one or more processing units that enables the control of the radiation beam source; and a direct feedback interface (DFI) control unit of claim 1, wherein the Cherenkov radiation is detected by the camera after exposure of a subject to high-energy radiation from the radiation beam source.

4. The system of claim 3, wherein the radiation beam source is a particle accelerator or other device for providing high-energy radiation.

5. The system of claim 3, wherein the radiation beam source may be cross-sectionally shaped by a beam-shaping apparatus.

6. The system of claim 5, wherein the beam-shaping apparatus is a multi-leaf collimator.

* * * * *